US009957485B2

(12) United States Patent
Kapre

(10) Patent No.: US 9,957,485 B2
(45) Date of Patent: May 1, 2018

(54) SYSTEMS AND METHODS FOR VIRUS PROPAGATION IN CELL CULTURES FOR VACCINE MANUFACTURE

(71) Applicant: Subhash V. Kapre, Bellevue, WA (US)

(72) Inventor: Subhash V. Kapre, Bellevue, WA (US)

(73) Assignee: Inventprise, LLC, Redmond, WA (US)

( * ) Notice: Subject to any disclaimer, the term of this patent is extended or adjusted under 35 U.S.C. 154(b) by 13 days.

(21) Appl. No.: 14/383,977

(22) PCT Filed: Apr. 5, 2013

(86) PCT No.: PCT/US2013/035385
§ 371 (c)(1),
(2) Date: Sep. 9, 2014

(87) PCT Pub. No.: WO2013/154928
PCT Pub. Date: Oct. 17, 2013

(65) Prior Publication Data
US 2015/0064768 A1    Mar. 5, 2015

Related U.S. Application Data

(60) Provisional application No. 61/621,533, filed on Apr. 8, 2012.

(51) Int. Cl.
| | | |
|---|---|---|
| A61K 38/47 | (2006.01) | |
| A61K 38/28 | (2006.01) | |
| A61K 38/46 | (2006.01) | |
| A61P 3/10 | (2006.01) | |
| C07K 14/62 | (2006.01) | |
| C12N 7/00 | (2006.01) | |
| C12M 1/00 | (2006.01) | |
| C12M 1/36 | (2006.01) | |

(52) U.S. Cl.
CPC ............... *C12N 7/00* (2013.01); *C12M 23/58* (2013.01); *C12M 41/48* (2013.01); *C12N 2760/20111* (2013.01); *C12N 2760/20152* (2013.01); *C12N 2760/20163* (2013.01)

(58) Field of Classification Search
CPC .... A61K 2300/00; A61K 38/28; A61K 38/47; A61K 47/02; A61K 9/0019
See application file for complete search history.

(56) References Cited

FOREIGN PATENT DOCUMENTS

| WO | WO 03/039459 | | 5/2003 |
|---|---|---|---|
| WO | WO03039459 | * | 5/2003 |
| WO | WO2003039459 | * | 5/2003 |

OTHER PUBLICATIONS

PCT Search and Patentability Report for PCT/US2013/035385, dated Jul. 24, 2013.

* cited by examiner

*Primary Examiner* — Barry A Chestnut
(74) *Attorney, Agent, or Firm* — Remenick PLLC

(57) ABSTRACT

The present invention provides a closed system to propagate virus-infected cells without the effect of shear force, while providing quicker access to nutrients than is available conventionally. This system design allows for a high density of infected cell growth to increase the virus yields and to maintain homogeneity of the contents of the main container. The system further provides a nuclease to degrade the cellular DNA prior for purification of the virus or viral components. As the system is designed for maximum containment at low risk, the live virus can be a hazardous virus such as a Bio-safety Level 3 (BSL 3), BSL 4 or BSL5 virus.

35 Claims, 3 Drawing Sheets

Figure 1:
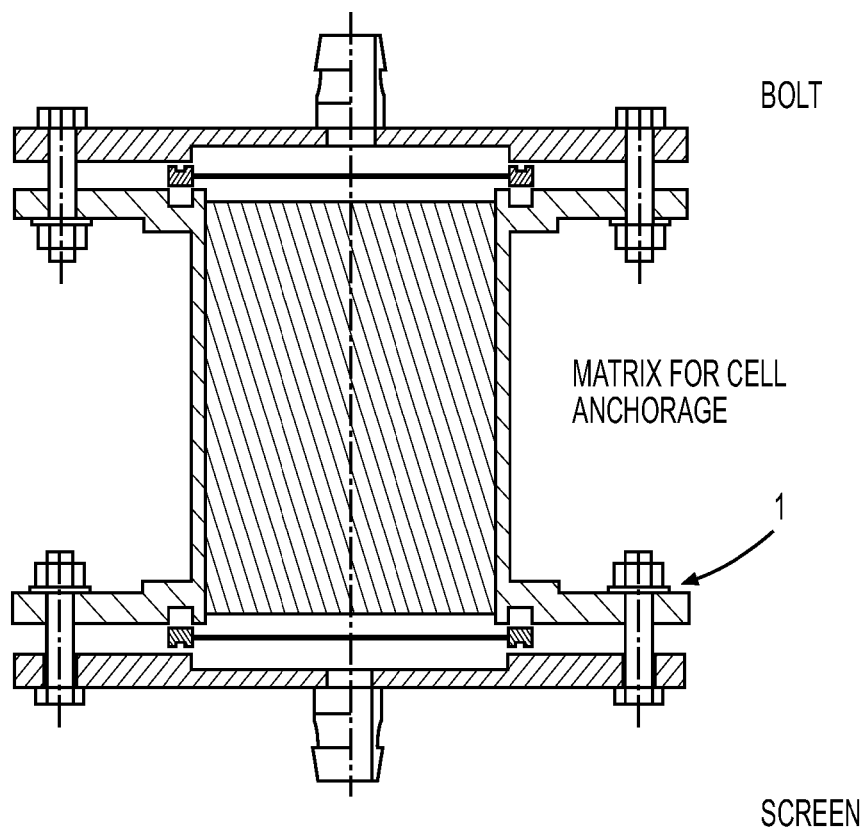

SYSTEMS AND METHODS FOR VIRUS PROPAGATION IN CELL CULTURES FOR VACCINE MANUFACTURE

REFERENCE TO RELATED APPLICATIONS

This application claims priority to U.S. Provisional Application No. 61/621,533 entitled "Systems and Methods for Virus Propagation in Cell Cultures" filed Apr. 8, 2012, the entirety of which is specifically incorporated by reference.

BACKGROUND

1. Field of the Invention

The invention is directed to the systems, components and methods for in vitro culturing of eukaryotic cells and, in particular, mammalian cells for the production of bulk quantities of virus. In addition, these systems, components and methods are useful for the propagation of virus from cell cultures by elimination of cellular DNA as well as residual proteins to obtain and isolate virus and viral components, preferably in an inactivated form, for the manufacture of vaccines.

2. Description of the Background

The ability to grow viruses and culture cells in vitro has been one of the single greatest advances in biology and medicine. Cell culturing has led to an understanding of the functions of cellular mechanisms, unraveling the processes cell-to-cell interactions, drug discovery and even the ability to develop and manufacture vaccines.

Currently, there are a great many variations in the in vitro culture of eukaryotic cells. Most advances in cell culture today are directed to addressing the specific requirements of one cell or tissue type. These advances include the use of incubators, capillaries, and micro-carriers, variations in culture media, cell-adhesion materials such as matrixes, the use of a movable bag referred to as a wave bioreactor and others (e.g., BioWave, Wave Bioreactor, BIOSTAT CultiBag, AppliFlex, Cell-Tainer, Tsnumai-Bioreactor, Optima, and Orbicell,). Each of these techniques addresses a unique problem encountered with a particular cell or tissue type. However, the basic concerns in achieving a successful cell culture after virus inoculation remains largely the same.

With all virus infected cells grown in vitro, there are at least six principle areas to be addressed: (i) appropriate starter cells are necessary; (ii) the critical mass of the cell culture needs to be determined; (iii) cells must be readily supplied with nutrients including necessary vitamins and minerals as well as oxygen; (iv) cell waste products must be efficiently removed; (v) stress on the cell cultures attributable to the incubation system should be minimized or eliminated, such as shear forces and hydrostatic pressures, (vi) sterility must be maintained throughout which includes complete separation from not only contamination in the form of bacteria and virus, but isolation from other cells and cell cultures. The infection of these cells with a virus for the purpose of manufacturing a vaccine adds the additional steps of inactivating the virus, the elimination of cellular DNA as well as residual proteins to obtain and isolate virus and viral components for a usable therapeutic vaccine and ensuring that the system operates in a safe manner for those working with potentially hazardous viruses.

The choice of appropriate cells for culturing and virus infection has remained a significant issue for decades. Currently, most virus infected cells obtained from a biological sample are maintained, if only for short periods of time. Many tissue types are harvested after growth and virus inoculation with the goal of seeking viable cell cultures. As yet there are no well-defined markers for determining viability in virus inoculated cell culture.

Supplying nutrients to the cells and removing cell waste products efficiently has been the subject of a great deal of research with much success. The issue of supplying nutrients such as carbohydrates, lipids, minerals, and vitamins has been successfully resolved by several techniques, such as, for example, hollow fiber technology. These and other advantages have been successfully incorporated into many cell culturing systems and techniques. However, the principles determining maximum cell mass after virus infection is closely related to the ability of the system to provide readily available nutrients including oxygen, and also remove waste products.

In the virus infected cell culture systems, stress on the cells should be minimized or eliminated. The presence of stresses, such as shear forces and hydrostatic pressures, greatly affects the efficiency of the culture system, and the amount of final virus yields derived which can increase from each run. Prior methods of reducing shear and hydrostatic forces include developing new oxygenation devices in order to reduce shear caused by bubbles, exploiting different protective agents, and modifying existing impellers and designing new types of agitators and immobilizing cells within a carrier matrix.

Conventional cell culture techniques typically involve a situation of no stress or stress. In the no stress situation, cells grow in relative stasis and without stress damage, but due to inadequate media exchange are less vigorous and proliferate poorly. In the stress situation, although the media exchange and removal of cell metabolites is good for vigorous cell growth, shear forces disengage the cells from anchorage surfaces and these detached cells perish which diminishes the amount of final viral yield.

The implementation of facile sterilization procedures for bioreactors and associated components is essential for clinical utility of inoculated virus cells to be used as a vaccine. The procedures for sterilization are well established, including standard methods both for sterilization of extracorporeal devices and for maintaining asepsis by standard in-line filters.

The inactivation of the cultured viral product is often achieved by solvent/detergent inactivation, pasteurization, pH activation or ultraviolet inactivation and chemical treatment. The inactivation method chosen often depends on the desired viral product. The solvent/detergent method is effective with viruses containing a lipid envelope, as the detergents used interrupt interactions between the molecules in the virus's lipid coating. As most enveloped viruses cannot live without their lipid coating, they die when exposed to these detergents. Common detergents used in this method include Triton-X 100. Pasteurization can also be effective if the desired proteins are ore thermally resistant than the viral impurities with which they are in solution. Certain proteins act as thermal stabilizers for viruses. Additionally, if the target protein is not heat-resistant, pasteurization could denature the target protein as well as the viral impurity. With pH inactivation, some viruses will denature spontaneously when subjected to low pH (acidic). This technique is useful if the target protein is more resistant to low pH than the viral impurity, and is generally more effective against enveloped viruses as opposed to unenveloped viruses. Ultraviolet inactivation can be used to induce the dimerization of nucleic acids within the virus. Once the DNA is dimerized, the virus particles cannot replicate their genetic material, preventing infection. Among the known chemical inactivation formaldehyde and Beta Propiolactone have been used for very many virus inactivations.

Vaccine Production

Each day, the human body is attacked by bacteria, viruses or other infectious agents. When an individual becomes infected with a disease causing agent, the body's built-in immune system attempts to defend against the foreign agent. When the body successfully defends itself, immunity against the infectious agent results. When the body's natural defenses fail to quell the attack, an infection can be the results. In the natural process of developing immunity, B cells produced by the body produce substances known as antibodies that act against the specific infectious agent and create a "log" of this experience that can be called upon for protection when exposed to the same infectious agent again months, years or even decades later. For subsequent times that the person encounters that specific infectious agent, circulating antibodies quickly recognize the infection and eliminate that infection from the body before signs of disease develop. It has been estimated that antibodies which can recognize as many as 10,000 different antigens or foreign infectious agents are circulating the blood stream.

A vaccine works in a similar manner in that it induces the body to generate an immunogenic response. However, instead of initially suffering the natural infection and risking illness in order to develop this protective immunity, vaccines create a similar protective immunity without generally exposing the body to a condition wherein an infection could occur.

Development of vaccines against both bacterial and viral diseases has been one of the major accomplishments in medicine over the past century. While conventional procedures have allowed for the development of effective vaccines for a number of diseases, these procedures have been ineffective for others. Thus a need remains for the development of safe and effective vaccines for a number of additional diseases.

Several basic strategies are useful in the manufacture of vaccines. One strategy is directed toward preventing viral diseases by weakening or attenuating a virus so that the virus reproduces very poorly once inside the body. Measles (Morbilliviruses virus), mumps (which can be viral or bacterial), rubella (Rubivirus or German measles) and chickenpox (varicella zoster virus) vaccines are made this way. Whereas natural viruses usually cause disease by reproducing themselves many thousands of times, weakened vaccine viruses reproduce themselves approximately 20 times. Such a low rate of replication is generally not enough to cause disease. Although the preparation of live, attenuated infectious agents as vaccines will often provide improved immunologic reactivity, such methods increase the risk that the vaccine itself will be the cause of infection, and that the attenuated organism will propagate and provide a reservoir for future infection. One or two doses of live "weakened" or attenuated virus may provide immunity that is life-long; however, such vaccines cannot be given to people with weakened immune systems.

Another method to manufacture viral vaccines is to inactivate the wild-type virus and use the inactivated materials to generate an immune response. By this method, viruses are completely inactivated or killed using a chemical. Killing the virus makes the virus unable to replicate in a body and cause disease. Polio, hepatitis A, influenza and rabies vaccines are made this way. The use of inactivated or killed bacterial or viral agents as a vaccine, although generally safe, will not always be effective if the immunogenic characteristics of the agent are altered. An inactive virus can be given to people with weakened immune systems, but may have to be given multiple times to achieve immunity.

Vaccines may also be made using parts of the virus. With this strategy, a portion of the virus is removed and used as a vaccine. The body is able to recognize the whole virus based on initial exposure to a portion of the virus. The hepatitis B vaccine for example, is composed of a protein that resides on the surface of the hepatitis B virus.

Thus, one must generally choose between an improved effectiveness and a greater degree of safety when selecting between the inactivation and attenuation techniques for vaccine preparation. The choice is particularly difficult when the infectious agent is resistant to inactivation and requires highly rigorous inactivation conditions which are likely to degrade the antigenic characteristics which help to induce an immune response and provide subsequent immunity.

In addition to the dead or weakened infectious agent, vaccines usually contain sterile water or saline. Some vaccines are prepared with a preservative or antibiotic to prevent bacterial growth. Vaccines may also be prepared with stabilizers to help the vaccine maintain its effectiveness during storage. Other components may include an adjuvant which helps stimulate the production of antibodies against the vaccine to make it more effective.

Methods to prepare vaccines today involve treating samples with glutaraldehyde or formaldehyde to fix or cross-link the cells or infectious particles. Such treatments generally involve denaturation of the native forms of the infectious particles. A disadvantage to this approach is that the protein coats of the infectious particles are damaged by this process, and thus may not be recognized by the immune system.

A clear need exists for a complete, modular, scalable system to handle large-scale bulk manufacturing of viruses including bio-safety level 3 viruses safely and efficiently. The problems with existing bioreactor designs include inadequate oxygenation, minimal capacity for the biological cell component, limited capability for removal of toxins, excessive shear and hydrostatic forces, and difficulty in transferring biosynthetic cell products for patient use. In addition, existing bioreactor designs have not dealt effectively with the diffusion-limited thickness of the cell mass, with providing a critical mass of cells, and with supplying oxygen throughout the length of the bioreactor.

Thus, there is a need for a composite apparatus that is able to carry out the entire process of cell growth, virus infection and propagation, purification and inactivation in a closed, low- or no-stress apparatus that maximizes cell growth and virus propagation, and increase throughput, recovery and safety.

SUMMARY OF THE INVENTION

The present invention overcomes the problems and disadvantages associated with current strategies and designs and provides new tools, systems and methods for the collection of cells and viruses.

One embodiment of the system is directed to methods of producing bulk quantities of inactivated virus from a population of adherent cells, comprising: providing a closed system that includes: one or more incubation vessels each of which contains matrix material; a media tank; pipes that channel media from the media tank to each of the incubation vessels; a valve downstream of the plurality of incubation vessels that, when activated, diverts the medium to a column; seeding the population of adherent host cells onto matrix material in each of a plurality of incubation vessels wherein each incubation vessel is operably connected to a media tank containing cell medium; providing a constant flow of cell medium from the media tank to the plurality of vessels, all in a closed system; inoculating the host cells with a live virus; allowing the live virus to replicate within the host cells; harvesting the host cells infected with the live virus; providing a DNAse or suitable enzyme to degrade the cellular DNA prior to purification; separating the live virus from the host cells in a column; eluting the virus from the column with a high salt solution; removing the high salt solution from the virus; and inactivating and isolated virus. Preferably the step of inactivation of the isolated virus is repeated 2 or more times. Preferably, the step of inactivating the isolated virus comprises mixing an inactivation agent into the isolated virus at a rate that precludes foaming. As the system is designed for low risk and maximum containment, preferably, the live virus is a bio-safety level 3 virus. Preferably, the step of eluting the virus from the high salt solution comprises a desalting media column, and further comprises regulating the flow through the closed system such that less than 1% of the cells in culture become unadhered during incubation. Preferably the flow rate through the system is 0.02-950 mls/hr. Preferably, the step of harvesting the host cells infected with the live virus comprises enzymatically degrading the host cellular DNA. Also preferably, the method further comprises passing the degraded host cells infected with the live virus through column packing material wherein the column comprises hydrophobic ion exchange material that specifically binds the live virus. Preferably, the live virus is separated from the host cells in an ion exchange column without adsorption of remnant protein or DNA and the method comprises at least two incubation chambers, more preferably at least four incubation chambers, and more preferably at least twenty incubation chambers. Also preferably, at least one incubation chamber is pre-seeded with cultured cells.

Another embodiment of the invention is directed to systems, preferably closed systems, for producing bulk quantities of an inactivated virus, comprising: at least one incubation chamber containing at least one permeable matrix; a media tank in fluid communication with the at least one incubation chamber; a virus capture loop in fluid communication with the media tank having an intake valve and an outflow valve; an intake valve control system coupled to the intake valve; an outflow valve control system coupled to the outflow valve; and a first inactivation tank in fluid communication with the virus capture loop. Preferably, the virus capture loop comprises an ion exchange column and/or at least one filtration column. Also preferably, the system comprises a second inactivation tank in fluid communication with the first inactivation tank and a plurality of incubation chambers stacked in parallel. The system preferably comprising a high salt solution tank in fluid communication with the media tank and the at least one permeable matrix comprises a porous polymeric material. Preferably the system comprises automated control systems to continuously monitor and adjust cell culture constituents and flow, and a virus storage device.

Figure 3:
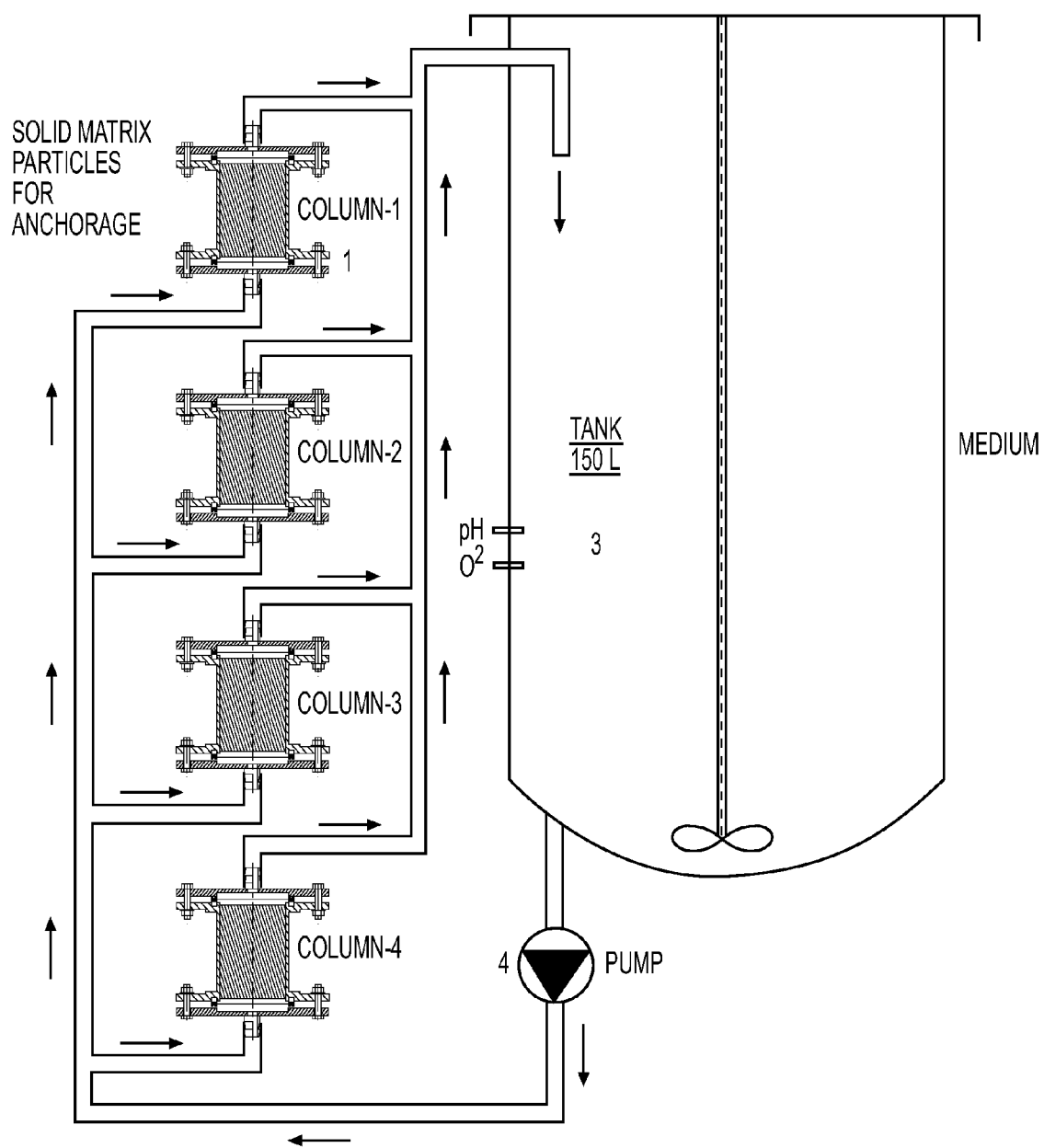
Figure 4:
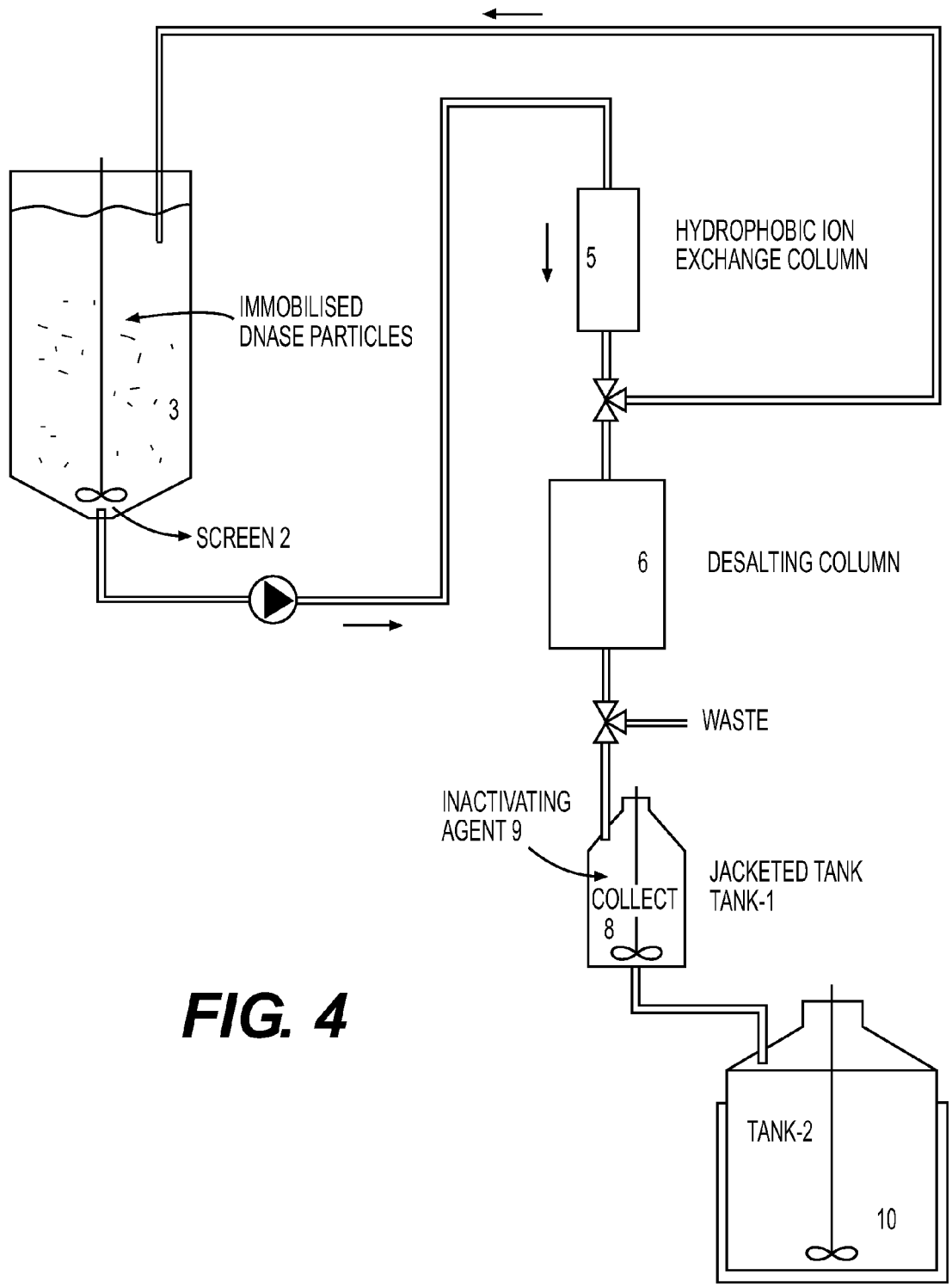

An advantage of the methods and systems of the invention is that cell propagation takes place absent the need for undue stresses on the cultured cells while providing the cells quicker access to nutrients than is available conventionally. This system design allows for a modular addition of incubators to increase the cell numbers attached to the main container, thereby increasing the capacity of the system. Another advantage of the invention is that the systems and methods are designed for transferring growing of cells on anchorage media to be shifted from a high stress area in a container to several containers with a screen at the bottom to keep the cells and the anchorage media in such containers which effectively reduce cell volume stacking to an optimum quantity necessary for to rapidly allow the exchange of media and waste without excess harmful pressures. The growing of viruses, the enzymatic degradation of cellular DNA, the collection of viruses free of cellular DNA, and the inactivation of the viruses is carried out in a closed condition. Virus infected cell growth is achieved in media packed columns placed one above another in multiples to act as modular infected cell growing partitions that rapidly increase the cell throughput. Another advantage of the invention is to provide a complete system to safely handle large-scale manufacture of hazardous virus such as, for example, bio-safety level 1 (BSL1), BSL2, BSL3, BSL4, or BSL5 viruses and a novel modular system for virus host cell culture that is economical, of low risk to users, and scalable.

Other embodiments and advantages of the invention are set forth in part in the description, which follows, and in part, may be obvious from this description, or may be learned from the practice of the invention.

DESCRIPTION OF THE FIGURES

FIG. 1 One embodiment of the invention of a column containing cell-attachment media.

FIG. 2 Another embodiment of the invention depicting a multiple stack system for scale up.

FIG. 3 Another embodiment of the invention depicting a virus collection column and also an inactivation system.

FIG. 4 A further embodiment of the invention detailing the recovery, purification and inactivation of the live virus.

DESCRIPTION OF THE INVENTION

The ability to grow cells in culture is critical to a great many aspects of microbiology and medicine, including the manufacture of vaccines. The parallel goals of achieving a maximum cell density with concomitant maximum cell viability are of primary consideration. However, as cells proliferate, the cell culturing system necessarily provides increasing resistance due to an inability of a conventional system to supply a consistent level of oxygen and nutrients to all cells, an inability to maintain an optimal pH, and an inability to quickly remove waste products. Typically, increased agitation of the media is performed to move greater amounts of nutrients across cell surfaces, but the shear forces created by the mixing in turn inhibit cell growth and can result in premature cellular death. Current techniques are directed toward achieving equilibrium between cell proliferation and cell death to achieve a culture of maximum viability. Accordingly, for every system there is a theoretical limit of cell density with maximum cell viability. For cells that are cultured for virus production, as virus growth is proportional to cell density, this maximum also limits the number of virus particles that can be recovered from infected cell cultures.

It has been surprisingly discovered that this equilibrium can be overcome and cells proliferated to a greater density while maintaining maximal viability. The present invention provides an integrated, closed cell culture system for the bulk growth of cells and preferably virus-infected cells in tissue culture and the subsequent collection of virus particles or viral components and, if desired, their inactivation. The design of the system includes one or more incubation vessels (1) containing growing cell cultures apart from a reservoir of cell culture medium (FIG. 1). Cell culture medium is transferred from the reservoir to the vessels through a series of conduits such as, for example, pipes or tubing (FIG. 3). This transfer is preferably by pumping culture medium from the reservoir through the pipes to the incubation vessels, thereby permitting each and every cell maximum access to the medium for absorption of nutrients, excretion of waste, and maintenance of a constant pH and temperature. The system is scalable through a wide range of volumes and adjustable due to the modular design. Preferably, the volume of the medium tank is equivalent to or greater than the volume of the incubation vessels. The system of the invention is not limited by cell type or structure and can be adapted to cells in suspension and cells that require adherence to a surface. When working with potentially infectious cells, such as virus-infected cells, the system also provides nearly complete safety to workers and other individuals from risk of infection or contamination. Cells are infected and harvested, virus concentrated in one or more columns, and thereafter inactivated and collected, all in a closed system (FIG. 4).

One embodiment of the invention is directed to a cell culture system (FIG. 3). The system comprises one or more scalable incubation chambers (1), a media reservoir (3) that supplies culture media individually to each of the incubation chambers (1), a pump (4) for transferring the cell culture medium from the tank to the incubation vessels and across the cell surfaces. Preferably the pump is a low-stress pump that does not shear or otherwise stress the cells. Preferably the pump has a flow rate of 0.02-950 mls/hr. Cell type and cell characteristics will be well-known to those skilled in the art to be able to determine the appropriate flow rate or flow rate can be determined empirically.

Figure 2:
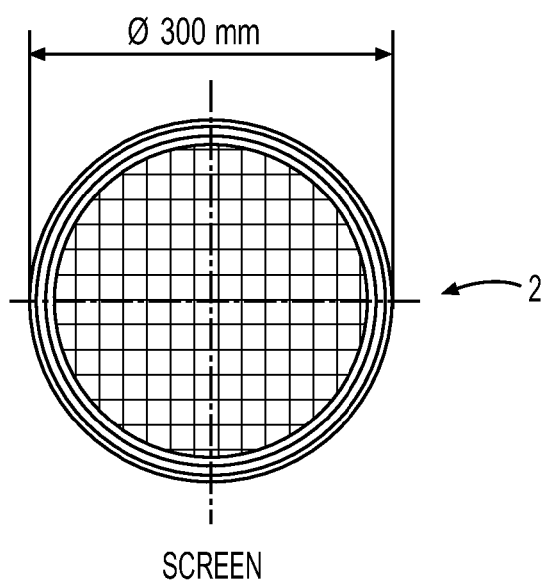

The incubation chambers (1) many be any size and shape as convenient, and are preferably from 10 to 600 cm in diameter and from 5 to 300 cm in height, and preferably about 30 by 30 cm, although other dimensions can be utilized as convenient to the system desired (FIG. 1). Also preferably, the incubation chambers have one or more porous or mesh surfaces with openings of preferably, between 0.1 mm and 100 mm, preferably between 1.0 mm and 100 mm, and also preferably not more than 4 mm, that are mounted on either side of the incubation chamber(s) (FIG. 2). Opening size will to some extent be determined by the cells and virus, and thus, can be determined by those skilled in the art or empirically. The mesh is preferably housed in a sterilize-able gasket material that is form fitted to seal the mesh in channels. The mesh is preferably secured to either end of the incubation chamber with end caps that have fluid ports. The incubation chamber is preferably filled with permeable matrices (2) capable of supporting cellular attachment and growth in a nutrient media rich environment. The matrix is selected to optimize the cellular attachment of host cells and can include porous polymeric materials in various sizes and shapes such as, for example, beads, films, sheets, semi-permeable membranes, porous beads, hollow fibers, tubes and other configurations suitable for cell culturing. The preferred matrix is selected for its ability to support host cells that are then infected with a virus and the capability to allow ease of detachment of the virus once optimal growth has been achieved. The porous mesh creates a false top and bottom that are capable of trapping the solid media on which the cells anchor and also tuning the flow of media through the incubation chamber ensuring the optimum rate of flow is achieved for cellular attachment to the matrices. Incubation chambers are preferably stackable, one above another, in a stand to meet output requirements. For example, a single incubation chamber may be used for experimental and research purposes, whereas commercial incubators may be preferentially larger allowing for the production of large quantities of biological material for vaccine manufacture. There can be any number of incubation chambers in this system preferably at least two, preferably at least four, preferably at least eight, preferably at least twelve, preferably at least twenty, preferably at least fifty, and preferably more as needed to meet the specific demands of the amount of final product needed such as, for example, virus particles. In addition, the systems and methods of the invention are equally useful for the production of whole virus or viral components such as the nucleic acids, specific proteins, viral walls, defective interfering particles, and envelope material or any component of the virus and/or component produced by the cell in response to virus contact and/or infection. The various components can be specifically chosen by selecting the particular cell culture conditions, nutrients, temperatures, pH values, host cells, growth cycle, incubation times and combinations thereof. The affinity column would contain an affinity material designed to bind to the chosen component if interest.

All of the incubation chambers can be connected to a central media tank (3) by way of flow and check valves, which may be one way if needed or desired to prevent back flow (FIG. 3). Several such stands provide multiple volumes that would enable the process to scale up in capacity. The media tank (3) design is preferably a sealed stainless steel vessel with a jacket and several intake and outlet ports connected by stainless steel pipes with the capacity needed to support the incubation chambers. However, other materials, such as glass, plastic, rubber, steel and other metals, carbon or other fibers, can be utilized in the media tank (3). For larger systems, metal is generally the desired material as it can be easily sterilized and re-used, whereas smaller systems would preferably comprise plastic or glass which also could be easily sterilized but then disposed. Preferably, the media tank contains a volume of media equal to or greater than the volume of the one or more incubation chambers. Also preferably, media tanks do not contain more than three times the volume of the incubation chambers for purposes of maintaining conditioned medium to the cells (i.e., medium that has been exposed to cells previously and therefore contains known and/or unknown cellular-derived components, but preferably retains sufficient nutrient content for continued cell propagation). The media tank (3) can have almost any capacity that is practical for the user, such, for example, 100 liters or more, 200 liters or more, 1,000 liters or more, or even greater volumes. The design of the media tank (3) preferably is optimized to allow the apparatus to be cleaned and sterilized in place. All transfer piping preferably possesses in-line valves at the ends with sterile connectors. Preferably, the vessel has automated control systems to continuously monitor and adjust cell culture constituents and flow. The system can be a closed loop system or an open loop system for custom additions or adjustments. Examples of preferred control systems include, but are not limited to, oxygenation apparatus with a dissolved oxygen (DO) measurement system, flow and mixer agitation, pH control system, nutrient monitoring and replenishment, temperature control, and volume control system. The media tank (3) preferably is also outfitted with infusion ports to allow addition of infectious viral agents in an aseptic manner to start the growth of the targeted virus within the cells in the incubation chambers (1). Preferably, the media tank (3) is also outfitted with a mixing or media agitation system that minimizes damage to the target virus when the virus is circulated through the media tank (3). The media tank (3) further preferably has the capability to activate an inline filter to collect virus and cellular degradation products.

The system preferably includes a virus capture loop that is normally closed when growing and infecting the host cells in the incubation chambers. When the virus laden media is ready for collection, the incubation chambers are rinsed (and can be flushed with additional media) into the media tank (3) (FIG. 4). The virus laden media, along with the cellular DNA degradation enzymes (e.g., DNAse and/or other nuclease(s)) are then agitated until the cellular DNA is degraded then passed through a media column to entrap viruses that have collected in the media tank (3). This column is preferably a hydrophobic ion exchange column optimized for trapping virus particles. While in this virus collection loop, preferably the media is continuously monitored and controlled to insure optimal virus collection. The hydrophobic ion exchange media only traps the virus, leaving behind in the media all cellular remnants including proteins and the added enzyme. There may also be employed additional filtration columns of different types and quantity in the loop to remove particulates specifically to act as an anti-fouling mechanism to protect and optimize virus collection on the hydrophobic ion exchange column.

On the intake side of the hydrophobic ion exchange column (5) there is preferably a valve control system that allows for the infusion of a self-generated high-salt solution to elute the trapped virus particles from the exchange column. When activated, the valve control system preferably precludes back flow into the media tank (3).

On the outflow side of the hydrophobic exchange column there is a valve control system that when activated, diverts the outflow which normally exits the column and returns to the media tank (3), and directs the outflow to a gel filtration desalting column (6). The outflow valve control system preferably has a diverter setting to divert waste and cleaning solutions to a holding tank during a cleaning and sterilization cycle.

When the virus is ready for collection, the intake valve of the hydrophobic ion exchange column (5) is activated and a high salt solution is infused from a separate solution tank. The solution tank is of sufficient construction to preclude oxidation of the surfaces due to the high salt concentration and may be polymeric or of sufficient stainless steel design. The solution tank is connected to the column (5) by an inline valve system. Prior to introduction of the high salt concentration eluent, an outflow valve from the ion exchange column is activated directing the detached virus into a gel media acting as a desalting column (6) to free the virus from the high salt solution. The virus fraction free of salt is then collected in a first stirred jacketed tank (8). Preferably, a virus inactivation agent is added to the first stirred jacketed tank (8) through a valve connected to tank (8) and the liquid is stirred in a controlled manner to preclude foaming.

To prevent live virus that may not have been inactivated from being treated, for example due to their presence in the intake piping to tank (8), the liquid is transferred to a second stirred jacketed tank (10), which is preferably sealed off from tank (8) by a cutoff valve. Additional inactivation agent can be added to tank (10) through a valve controlled infusion port. As only the inactivating agent and mixed virus enters the second tank the possibility of any virus remaining un-inactivated is removed. The end of the intake tube is preferably designed to allow liquid to flow down the sidewall avoiding foaming as the liquid enters the tank (10). During the virus production process, preferably the entire system is sealed and the production sequence is performed in an aseptic manner in a closed system without hazardous exposure of processing personnel during the processing. Thus, inactivated bulk virus can be handled safely prior to testing or dispensed into large or small aliquots for storage. Preferably, the complete system can be systematically isolated and cleaned using processes known to a person of skill in the art.

Another embodiment of the invention is directed to methods to manage the optimized growth of virus using the closed system of the invention. Production of bulk quantities of inactivated virus in this continuous closed system is a batch process that includes several sequential steps. To start the sequence, host cells to support growth of live virus are seeded into a bioreactor loop that includes a large media tank (3) and preferably multiple stacked cell culture incubation chambers (1). The incubation chamber design and control of the flow of the media are preferably optimized to minimize the shearing effects found in traditional bioreactors. When the seeded cells have reached the maximum packed cell density, these cells are inoculated with a live virus. The live virus is preferably injected through an injection port into the media tank (3) through which the virus flows into the incubation chambers. The virus is allowed to replicate in the incubation chambers until the virus has fully populated the host cells and is ready for collection. The virus is then harvested from the bioreactor incubation chambers and sent into the media tank (3) where the virus and fragments of the host cells and cellular DNA are captured and held in the tank which inhibits the flow the components back through the incubation chambers through the valve control The next step of the batch process includes directing the flow of captured live virus through a column system, which may include a hydrophobic ion exchange column or other suitable filtration column (5), after closing off the bioreactor incubation chambers from the media tank (3) with cutoff valves and opening the retention filter from the outflow port of the media tank (3). The column (5) is connected back to the media tank (3) through a valve system that allows flow in only one direction. The function of the column (5) is to capture the target live virus from the flowing media.

After capturing the live virus in the column (5), the next step is to elute the virus from the column packing material. This step includes removing the media tank (3) from the loop by shutting off the intake valve to the column (5) and directing the return flow to the desalting column (6). The desalting column (6) is connected to a first stirred jacketed tank (8). A high salt concentration eluent solution is generated and introduced to the intake side of the hydrophobic ion exchange column (5) through the valve system from a separate holding tank and allowed to elute the substantially purified virus into the desalting column (6). The high salt solution is passed into a gel filtration desalting column that removes the high salt concentration from the purified virus and directs the outflow into the first stirred jacketed tank (8) where the now depleted salt, virus-containing solution is held until initiation of the inactivation step.

The first stirred jacketed tank (8) is then isolated from the columns through a cutoff valve and a virus inactivation agent (9) is added through a valve into the tank (8) where the inactivation agent (9) is gently mixed to preclude foaming. After the first inactivation step the contents of the tank are transferred to a second tank (10) where this process may be repeated to insure complete inactivation of virus. At the conclusion of this step the inactivated bulk virus is ready for testing and packaging. The invention involves vigorous exchanges as well as avoidance of shears thus promoting high growth. Due to media entrapment, added protein can be removed prior to infection thus avoiding losses in purification.

The gentle moving of nutrients through the solid matrix, which has cells attached thereto, provides the cells a chance to replenish nutrients and expel waste without affecting their weakened adhering ability. Thus infected cells remain attached and viable for a longer time and are able to generate virus particles in a larger quantity. The sterilizable DNAse affinity media is in the media tank (3). The enzyme thus has a continuous chance of degrading the formed DNA thereby lowering its presence as a whole molecule and allowing for removal by simple separation chromatography.

The virus is collected in a hydrophobic ion exchanger where no adsorption of protein or DNA takes place. The column is washed and the attached virus eluted by a high salt buffer. The eluted fraction is sent into a gel filtration column through a valve diverter to free the virus of high salt. Such salt free virus fraction is mixed with inactivating agents such as, for example, formaldehyde or beta propiolactone. After a thorough mixing, the solution is transferred to another tank. This ensures that all liquid in the second tank has a virus solution mixed with the inactivating agent.

Another embodiment of the invention is directed to methods of producing bulk quantities of virus for the production of a vaccine, preferably a vaccine that provides immunity against the virus. The method comprises providing a closed-loop cell culture system that includes one or more incubation vessels each of which contains a population of cells, one or more media tanks containing cell culture media connected to the one or more incubation vessels, wherein the cell culture media flows from the one or more media tanks to the one or more incubation vessels and back to the one or more media tanks, and a valve downstream of the one or more incubation vessels that, when activated, closes a connection to the one or more media tanks and opens a connection to a column containing an affinity material, wherein the column possesses an input end connected to the one or more incubation vessels and an output end connected to a collection vessel. A population of cells is added to the one or more incubation vessels and infected cells with virus or a population of virus-infected cells is added. Cells may be adherent cells, partially adherent cells or cells in suspension that are maintained in the incubation vessel by a matrix material or a semi-permeable membrane. Preferred cells include human or primate cells, infected or uninfected cells, cells with virus sequences integrated into their genome, primary cells or cells adapted to cell culture, immortalized cells, cells that do not require subsequent infection (although multiple infections may be performed), epithelial cells, myeloid cells, pluripotent or stem cells, differentiated, partially differentiated or undifferentiated cells, hybrid cells (from multiple types or species), tumor cells, embryonic or neonatal cells, human, MRC-5 cells or any combination thereof including combinations of different cells. Virus infection may not be necessary, for example, with cells are previously infected or contain integrated virus. Virus infection is also not necessary when working entirely with uninfected cells when harvesting cellular components. Cell culture medium flows from the media tanks to the incubation vessels within the closed-loop cell culture system for a time period that allows for the replication of quantities of virus. The time period is preferably the period of time needed for culturing the virus-infected cells to generate replicated virus. The time period is preferably at least one day, preferably at least two days, preferably at least five days, preferably at least ten days, preferably at least two weeks, preferably at least three weeks, preferably at least four weeks, and preferably at least six weeks. More preferably the time period is from two days to two weeks. The valve is activated one or more times during the period of cell culture such that replicated virus flows to the column under conditions that promote the selective binding of replicated virus to the affinity material. Preferably the valve is activated periodically and at time of virus expression from the infected cells. There may be a single period of virus expression such as when the virus destroys the host cell, or multiple or continuous periods when the virus does not destroy host cells or only infects a portion of the population of cells at a particular stage of growth and/or proliferation such as at the M, S, G1 and/or G2 stage. In systems where there is only one period of virus expression, preferably the cells are cultured to maximal production of virus. At or shortly after maximal production, the valve is activated diverting fluid to the column. In systems where there are multiple periods of virus expression, preferably the cells are cultured and at each period of maximal expression, the valve activated diverting fluid to the column. The same or different columns can be used for each collection cycle. In systems where there is continual virus expression, preferably cell cultures are maintained and the virus affinity column is an integral part of the closed system such that cell culture media is continually passing through the column capturing virus. With each system, virus is eluted from the affinity material and collected in a collection vessel. Eluted virus is then treated to inactivate and render the virus non-infectious and suitable for safe handling and use in the manufacture of a vaccine. Inactivation steps are preferably performed at least once, at least twice, or at least three times or more.

Although the systems and methods of the invention are useful for growth of any virus, the inventions are preferred for the manufacture of bio-safety level 3 virus (BSL 3 virus), BSL 4 virus, and/or BSL 5 virus and combinations thereof in part because the system is self-contained and requires minimal to no handling of live virus by skilled technicians. Cells that can be used in the systems and methods of the invention include suspension cells, adherent cells and partially adherent cells. Preferred cells include human cells, primate cells, MRC5 cells, PM3218 cells, and combinations thereof.

The following examples illustrate embodiments of the invention, but should not be viewed as limiting the scope of the invention.

EXAMPLES

Example 1: Growth of Rabies Virus

Host cell MRC-5 were maintained routinely in tissue culture flasks (Corning, Corning N.Y.) in Dulbecco's Modified Eagle's Medium (DMEM) with 4.5 g/l glucose supplemented with 10% Fetal Bovine Serum. Retroviral vector producer cell line PM3218 was routinely maintained in tissue culture flasks (Corning, Corning N.Y.) in Dulbecco's Modified Eagle's Medium with 4.5 g/l glucose absent Fetal Bovine Serum. 20 L of DMEM with 10% fetal bovine serum (FBS) was used as the cell culture medium for the bioreactor. Cytodex 1 microcarrier beads (Sigma-Aldrich, St. Louis Mo.) sterilized and washed according to the manufacturer's instructions, were loaded into the incubation chambers as the anchorage media.

Host cell MRC-5 were seeded in the incubation chambers at a concentration of $3 \times 10^9$ and were fed continuously with 20 L of culture medium at a temperature of 37° C. for four days, or until the host cell concentration had reached $3\times10^{10}$ or the maximum packed cell density that can be supported by each individual incubation chamber. At this time, retroviral cell line PM 3218 was introduced to the media tank (3) through an injection port into the media tank (3) and allowed to flow into the incubation chambers. The viral cell line was then allowed to replicate in the incubation chambers until the virus has fully populated the host cells and the host cells are ready for collection and deactivation.

Once the host cells were fully inoculated with the virus, the cells were sent into the media tank (3) where the virus and host cells were captured and held by a 0.2 m filter unit (Millipore) that prevents the flow of the virus infected host cells back through the incubation chambers. The live virus was then directed to the hydrophobic ion exchange media column which was connected back to the media tank (3) through a valve system that only allows flow in one direction. The hydrophobic ion exchange column captures the live virus from the media. The virus was then eluted from the column packing material by removing the media tank (3) from the closed loop by shutting off the intake valve and introducing a high salt solution reservoir directing the return flow to the desalting column. The desalting column was connected to a first collection tank after a high salt concentration eluent solution is generated and introduced to the intake side of the ion exchange column through the valve system from a separate holding tank and allowed to elute the substantially purified virus into the desalting column. The high salt solution was passed into a HIPREP™ 26/10 Desalting Column (GE Healthcare) that removed the high salt concentration from the purified virus and directed the outflow into the first inactivation tank where the solution was held until the inactivation step could be initiated.

The first inactivation tank was then isolated from the columns through a cutoff valve and beta propiolactone was added through a valve, into the tank where the beta propiolactone was gently mixed to preclude foaming. After the first inactivation step the contents of the tank were transferred to a second tank where this process was repeated to insure complete inactivation of virus. At the conclusion of this step the inactivated bulk virus was ready for testing and packaging. It was surprisingly discovered that as opposed to the current standard methods of growing and harvesting viruses, this method yielded on average 3 times more final vaccine doses than conventional methods.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of producing bulk quantities of inactivated virus comprising:

providing a closed-loop cell culture system that includes:

a plurality of incubation vessels stacked one above another, each of which contains a permeable mesh affinity matrix material for supporting a population of adherent cells, each incubation vessel having at least one mesh surfaces secured to either end of the incubation vessel;

a media tank containing cell culture media connected to the incubation vessels, wherein the cell culture media flows from the media tank to the incubation vessels and back to the media tank, wherein the flow rate of the cell culture media through the system is from about 100 mls/lar to about 950 mls/hr, wherein the media tank has a volume not more than three times the volume of the incubation vessels;

a mixing system within the media tank; and a valve downstream of the incubation vessels that, when activated, closes a connection to the media tank and opens a connection to a column, wherein the column possesses an input end connected to the incubation vessels and an output end connected to a collection vessel;

contacting the population of adherent cells to the permeable mesh affinity matrix material contained within the one or more incubation vessels;

flowing the cell culture medium within the closed-loop cell culture system for a first period of time, wherein flow of cell culture media through the system is at a rate such that less than 1% of the adherent cells become un-adhered during the first period of time;

injecting a live virus into the media tank to inoculate the population of adherent cells with live virus creating virus infected cells;

culturing the virus-infected cells for a second period of time to generate replicated virus;

adding an agent to the virus-infected cells after the second period of time to promote isolation of replicated virus from the virus-infected cells;

activating the valve such that replicated virus flows to the column under conditions that promote the selective retention of replicated virus;

removing the media tank from the closed-loop cell culture system and directed the flow to a desalting column;

eluting the replicated virus in the desalting column and collecting virus in the collection vessel;

inactivating the eluted virus in a first jacketed tank;

repeating the inactivation in a second jacketed tank;

collecting the inactivated bulk virus.

2. The method of claim 1, wherein the live virus is a bio-safety level 3 virus.

3. The method of claim 1, where the population of adherent cells comprise human cells, primate cells, MRC5 cells, PM3218 cells, or combinations thereof.

4. The method of claim 1, wherein the plurality of incubation vessels comprises at least four incubation vessels.

5. The method of claim 1, wherein the plurality of incubation vessels comprises at least twenty incubation vessels.

6. The method of claim 1, wherein the plurality of incubation vessels is pre-seeded with adherent cells.

7. The method of claim 1, wherein the media tank contains an access port that allows for the addition or removal of cell culture media.

8. The method of claim 1, wherein the media tank does not contain an access port that allows for the addition or removal of cell culture media.

9. The method of claim 1, wherein the closed-loop cell culture system contains at least 20 L of cell culture media.

10. The method of claim 1, further comprising a second media tank containing cell culture media and a second valve that, when activated, closes the connection to the media tank and opens a connection to the second media tank.

11. The method of claim 1, wherein the permeable mesh affinity matrix within the column comprises hydrophobic or hydrophilic ion exchange media.

12. The method of claim 1, wherein the first period of time is from two days to two weeks.

13. The method of claim 1, wherein the second period of time is from two days to two weeks.

14. The method of claim 1, wherein the agent comprises one or more of a cell lysing chemical, an enzyme, a surfactant, a detergent, a reducing agent, a chelating agent, or an agent that alters pH.

15. The method of claim 14, wherein the enzyme is a nuclease that acts upon cellular DNA.

16. The method of claim 1, wherein the permeable mesh affinity matrix does not preferentially adsorb protein or DNA.

17. The method of claim 1, wherein the permeable mesh affinity matrix preferentially binds replicated virus.

18. The method of claim 1, wherein the step of inactivating the eluted virus comprises mixing an inactivation agent with the eluted virus such that the eluted virus is rendered non-infectious.

19. The method of claim 18, wherein the mixing is performed at a rate that precludes foaming.

20. A method of producing bulk quantities of inactivated virus comprising:
   providing a closed-loop cell culture system that includes:
      a plurality of incubation vessels stacked one above another each of which contains a population of cells, each incubation vessel having at least one mesh surfaces secured to either end of the incubation chamber;
      one or more media tanks containing cell culture media connected to the incubation vessels, wherein the cell culture media flows from the one or more media tanks to the incubation vessels and back to the one or more media tanks, wherein the media tank has a volume not more than three times the volume of the incubation vessels; and
      a valve downstream of the incubation vessels that, when activated, closes a connection to the one or more media tanks and opens a connection to a column containing a permeable mesh affinity matrix material, wherein the column possesses an input end connected to the one or more incubation vessels and an output end connected to a collection vessel;
   adding the population of cells to the one or more incubation vessels and infecting the cells with virus or adding virus-infected cells to the one or more incubation vessels;
   flowing the cell culture medium within the closed-loop cell culture system, wherein the flow rate of the cell culture media through the system is from about 100 mls/hr to about 950 mls/hr such that less than 1% of the adherent cells become un-adhered;
   culturing the virus-infected cells for a period of time to generate replicated virus;
   activating the valve one or more times during the period of time such that replicated virus flows to the column under conditions that promote the selective binding of replicated virus to the permeable mesh affinity matrix material;
   eluting the replicated virus from the affinity material and collecting virus in the collection vessel; and
   inactivating the eluted virus to render the virus non-infectious and suitable for manufacture of a vaccine.

21. The method of claim 20, wherein the live virus is a bio-safety level 3 virus.

22. The method of claim 20, where the population of adherent cells comprise human cells, primate cells, MRC5 cells, PM3218 cells, or combinations thereof.

23. The method of claim 20, wherein the plurality of incubation vessels comprises at least four incubation vessels.

24. The method of claim 20, wherein the one or more media tanks do not contain an access port for the addition or removal of cell culture media.

25. The method of claim 20, further comprising a second media tank containing cell culture media and a second valve that, when activated, closes the connection to the media tank and opens a connection to the second media tank.

26. The method of claim 20, wherein the affinity material within the column comprises hydrophobic or hydrophilic ion exchange media.

27. The method of claim 20, wherein the period of time is from two days to four weeks.

28. The method of claim 20, wherein the inactivating comprising adding an inactivating agent at a rate that precludes foaming.

29. The method of claim 20, further comprising one or more repetitions of the virus inactivation step.

30. A closed system for producing bulk quantities of inactivated virus, comprising:
   a plurality of incubation chambers stacked one above another and containing at least one permeable mesh matrix secured to either end of each incubation chamber for supporting a population of cells;
   a media tank for maintaining cell culture medium in fluid communication with the at least one incubation chamber, wherein the flow rate of the cell culture media through the system is from about 100 mls/hr to about 950 mls/hr such that less than 1% of the adherent cells become un-adhered, wherein the media tank has a volume not more than three times the volume of the incubation vessels;
   a mixing system within the media tank;
   a virus capture loop in fluid communication with the media tank having an intake valve and an outflow valve;
   an intake valve control system coupled to the intake valve;
   an outflow valve control system coupled to the outflow valve;
   a virus inactivation vessel in fluid communication with the virus capture loop; and
   automated control systems and software for monitoring and adjusting one or more components of the cell culture medium and fluid flow.

31. The system of claim 30, wherein the virus capture loop comprises an ion exchange column.

32. The system of claim 30, wherein the virus capture loop comprises at least one filtration column.

33. The system of claim 30, further comprising a second inactivation tank in fluid communication with the first inactivation tank.

34. The system of claim 30, further comprising a high salt solution tank in fluid communication with the media tank.

35. The system of claim 30, wherein the at least one permeable mesh matrix comprises a porous polymeric material.

* * * * *